United States Patent [19]

McDougald

[11] 4,061,755

[45] Dec. 6, 1977

[54] COCCIDIOCIDAL COMBINATION OF MONENSIN AND METICHLORPINDOL

[75] Inventor: Larry R. McDougald, Greenfield, Ind.

[73] Assignee: Eli Lilly and Company, Indianapolis, Ind.

[21] Appl. No.: 670,485

[22] Filed: Mar. 25, 1976

[51] Int. Cl.$^2$ .................. A01N 9/02; A61K 31/44
[52] U.S. Cl. ........................ 424/263; 424/115; 424/283
[58] Field of Search ................... 424/115, 263, 283

[56] References Cited

U.S. PATENT DOCUMENTS

| | | | |
|---|---|---|---|
| 3,246,001 | 4/1966 | Rigterink | 260/297 |
| 3,501,568 | 3/1970 | Haney et al. | 424/115 |

*Primary Examiner*—V. D. Turner
*Attorney, Agent, or Firm*—William E. Maycock; Joseph A. Jones; Everet F. Smith

[57] ABSTRACT

The combination of monensin and meticlorpindol is synergistically effective in the control of coccidiosis of poultry.

5 Claims, No Drawings

COCCIDIOCIDAL COMBINATION OF MONENSIN AND METICHLORPINDOL

BACKGROUND OF THE INVENTION

This invention belongs to the field of poultry husbandry and provides new methods and compositions for the control of coccidiosis of poultry. The damage done by coccidiosis is well known. All of the economically reared poultry species are subject to infections of coccidia, which cause severe losses unless controlled. Coccidial infections not only cause the infected birds to gain weight more slowly than normal, and to convert their feed inefficiently, but often result in the deaths of large numbers of birds.

Like most parasitic infections, coccidiosis is most frequent and most damaging in flocks of birds reared in conditions of high population density. Since these conditions are also the most economical, modern efficient poultry operations are very likely to suffer severely from coccidiosis.

The two coccidiocides which are used in this invention are presently known in the animal health art. The novelty of the present invention resides in the discovery that the compounds, when combined in proper amounts or concentrations, are synergistic. The coccidiocidal effect of the combination is greater than the effect which could be expected from the known effects of the components of the combination, when used alone. Thus, use of the combination allows the poultry grower to obtain economically satisfactory coccidiocidal effect with the administration of unusually small amounts of the coccidiocides. Small dosages have the obvious economic benefit, and also are likely to result in reduced residues of coccidiocide in the edible tissues of the poultry.

SUMMARY OF THE INVENTION

This invention provides a coccidiocidal composition for poultry comprising coccidiocidally-ineffective concentrations of monensin and of meticlorpindol, which coccidiocides are synergistically coccidiocidally effective in combination, together with a poultry feedstuff or drinking water.

The preferred concentrations of the coccidiocides are from about 35 to about 65 parts per million by weight (ppm.) of monensin and from about 20 to about 70 ppm. of meticlorpindol. The particularly preferred concentrations of the coccidiocides are about 50 ppm of monensin and from about 30 to about 60 ppm of meticlorpindol.

This invention also provides a coccidiocidal method for poultry which comprises orally administering to the poultry a composition as described above, wherein the composition provides the poultry's entire food or drinking water supply.

DESCRIPTION OF THE PREFERRED EMBODIMENT

All concentrations, ratios, amounts and percentages mentioned herein are in weight units. Temperatures are on the Celsius scale.

The compounds used in this invention have long been known in the animal health art. References which describe the coccidiocides and their preparations will be named. The disclosures of the references are herein incorporated by reference.

Monensin is described in U.S. Pat. No. 3,501,568, where it is called A3823 complex. As the patent explains, the production of monensin by fermentation produces a mixture of factors, all of which are coccidiocidal and all of which are usuable in this invention. As is usual in the art, the term "monensin" is used here to refer to the unresolved mixture of factors produced by fermentation.

Another patent, U.S. Pat. No. 3,832,358, shows a modified form of monensin known as deshydroxymethylmonensin, which is likewise functional in the present invention.

Meticlorpindol, 3,5-dichloro-2,6-dimethyl-4(1H)-pyridinol, is described by U.S. Pat. No. 3,246,001, of Rigterink.

The monensin molecule has hydroxyl groups, which may be esterified to form acyl esters. Such esters, particularly the $C_2$—$C_6$ alkanoyl esters, are used in the present invention. Esterification occurs at one or more of the hydroxyl groups upon simple treatment with a $C_2$—$C_6$ carboxylic acid anhydride or acid halide, for example, at room temperature in methanol.

Monensin, the acyl esters thereof, and deshydroxymethylmonensin form physiologically-acceptable salts. Representative alkali metal and alkaline earth metal salts include the sodium, potassium, lithium, cesium, rubidium, barium, calcium and magnesium salts.

Suitable amine salts include the ammonium and the primary, secondary and tertiary $C_1$—$C_4$ alkylamine and $C_2$—$C_4$ hydroxyalkylamine salts. Illustrative amine salts include those formed by reaction with ammonium hydroxide, methylamine, s-butylamine, isopropylamine, diethylamine, diisopropylamine, ethanolamine, triethylamine, 3-amino-1-propanol and the like.

The salts are prepared according to the general procedures commonly employed for the preparation of cationic salts. For example, the free acid form of the compound is dissolved in a suitable solvent, and an aqueous or organic solvent solution of the desired base is added to the solution. The salts are isolated by filtration or by evaporation of the solvent.

It is well known in the veterinary pharmaceutical art that conditions within the treated animal or bird frequently change a compound to chemical forms other than that in which it was administered. Therefore, the form in which it may be administered does not affect the method of treatment and may be chosen for reasons of economics or convenience. Monensin, therefore, may be administered in the form of any desired alkanoyl ester or salt without effect on the efficacy of the invention.

Accordingly, the word "monensin" is used herein to refer to the various factors of monensin, and the alkali metal, alkaline earth metal, ammonium and primary, secondary and tertiary $C_1$—$C_4$ alkylamine and $C_2$—$C_4$ hydroxyalkylamine salts thereof. It will be understood that other forms of monensin, including deshydroxymethylmonensin, the $C_2$—$C_6$ alkanoyl esters of monensin, and the salts of the esters and of deshydroxymethylmonensin, are equivalent and also may be used in this invention.

The present invention has been tested by in vivo experiments with chickens infected with coccidiosis. The following tests are exemplary of the efficacy of various compositions and methods of the invention. In the tests described below, monensin was used as the sodium or mixed sodium-potassium salt of the unresolved mixture of factors produced by fermentation.

Untreated, infected control birds and untreated normal control birds were used in all experiments described below. The birds used were from a homogeneous research flock, and the *E. tenella* culture used to infect the birds was from a laboratory strain known to reproduce consistently and to produce uniform infections. The coccidiocides were mixed with the birds' feed in concentrations, measured in ppm., shown in the tables below.

The extent of coccidial infection is expressed as a lesion score on an 0-4 scale. At the end of the tests, all birds were killed, and their intestinal tracts were examined. Birds which showed none of the lesions left by coccidia were scored 0, and birds with extremely severe infections were scored 4. Intermediate degrees of infection were given lesion scores of 1, 2 or 3. The scores of all birds which received a given treatment were averaged.

Test 1

One-week-old broiler chicks were allotted to five-bird cages and were fed medicated or control ration for one day prior to infection with 50,000 oocysts of *Eimeria tenella* per bird. The chicks were maintained on the same rations for seven days and infections were scored as described above. Each treatment group comprised four 5-bird cages.

| Treatment | Concentration | Lesion Score |
|---|---|---|
| None | 0 | 2.5 |
| monensin | 50 | 1.2 |
| meticlorpindol | 30 | 3.3 |
| meticlorpindol | 60 | 2.4 |
| monensin + meticlorpindol | 50 + 30 | 1.4 |
| monensin + meticlorpindol | 50 + 60 | 0.7 |

Test 2

This test was conducted in the same fashion as the test above, except that each chick was inoculated with 100,000 sporulated oocysts.

| Treatment | Concentration | Lesion Score |
|---|---|---|
| None | 0 | 3.8 |
| monensin | 50 | 2.7 |
| meticlorpindol | 30 | 3.6 |
| meticlorpindol | 60 | 3.0 |
| monensin + meticlorpindol | 50 + 30 | 2.2 |
| monensin + meticlorpindol | 50 + 60 | 1.4 |

The present invention is useful to protect poultry in general. Not only such barnyard fowl as chickens, turkeys, ducks and geese may be protected thereby, but also exotic fowl such as pheasants and quail.

Coccidiosis is likely to affect poultry of any age and in any type of cultural practice. The present invention, therefore, may be used at any time to protect poultry from coccidiosis. As noted above, however, coccidiosis is most likely to affect poultry being reared in confined quarters, as in broiler houses and the like. Use of the invention in poultry reared under such conditions, therefore, will provide particularly great benefits.

Since coccidiosis is likely to break out at any time, use of this invention is recommended at any time of year and may be continued for any length of time. Continuous administration of a composition of this invention throughout the lives of the poultry is a particularly useful embodiment of the invention. However, the administration of a composition of this invention for even short periods of time, such as a few days, will also produce benefits and is a useful manner in which to carry out the method of this invention.

The compositions and methods of this invention are used for the control of coccidiosis in the usual fashion. Coccidiosis of poultry directly affects the intestinal tract, and anticoccidial drugs are therefore administered orally. The compositions of this invention, accordingly, are compositions wherein the synergistic coccidiocides are combined with either a poultry feedstuff or with drinking water. The compositions are novel only because of the presence therein of the synergistic coccidiocides, and otherwise follow conventional practices in the feedstuff industry.

The concentrations of the coccidiocides which are named herein are based on food or drinking water compositions which are the entire food or drinking water supply of the poultry. This method of describing the concentrations of the coccidiocides is in accordance with the practice of the poultry industry, since it is normal to supply to poultry only one source of food and one source of drinking water. Those of skill in poultry husbandry will recognize, however, that the concentrations must be adjusted upward, should it be desirable to supply the poultry with various sources of food or water, only part of which are compositions of this invention.

Poultry feedstuffs made according to all formulae and manners used in the poultry industry are perfectly satisfactory as carriers for the synergistic coccidiocides of this invention. The following poultry feedstuff formulae are representative of formulae typically used in the industry and are listed to assist the reader. A poultry scientist or grower will understand from inspection of the following formulae, however, that the formulation of the poultry feedstuff is not a limiting factor in the use of this invention. Feedstuffs based on any grain and containing any vitamin concentrate, mineral concentrate or other drugs and feed additives are perfectly satisfactory. Both conventional dry and pelleted feeds and liquid suspension feeds including feeds based on distiller's wastes and milk byproducts may be used in the compositions of this invention.

| Turkey Starter | |
|---|---|
| Ingredients | Percent |
| soybean meal, solvent extracted dehulled | 40.7 |
| corn, yellow, ground | 39.7 |
| fish meal with solubles | 5.0 |
| beef tallow | 5.0 |
| corn distillers dried solubles | 2.5 |
| alfalfa meal, dehydrated (17%) | 2.5 |
| dicalcium phosphate feed grade | 2.5 |
| calcium carbonate | 1.2 |
| vitamin premix [1] | 0.5 |
| salt (NaCl) | 0.2 |
| trace mineral premix [2] | 0.1 |
| methionine hydroxy analog | 0.1 |
| Total | 100.0 |

| Turkey Finisher | |
|---|---|
| Ingredients | Percent |
| corn, yellow, ground | 71.2 |
| soybean meal, solvent extracted, dehulled (50%) | 9.9 |
| corn distillers dried solubles | 5.0 |

-continued
Turkey Finisher

| Ingredients | Percent |
|---|---|
| alfalfa meal, dehydrated (17%) | 5.0 |
| animal fat | 3.0 |
| fish meal with solubles | 2.5 |
| dicalcium phosphate, feed grade | 1.7 |
| calcium carbonate | 0.5 |
| vitamin premix [1] | 0.5 |
| salt (NaCl) | 0.4 |
| methionine hydroxy analog | 0.2 |
| trace mineral premix [2] | 0.1 |
| Total | 100.0 |

Chick Starter Light Breeds

| Ingredients | Percent |
|---|---|
| corn, yellow, ground | 56.3 |
| soybean meal, solvent extracted, dehulled (50%) | 17.9 |
| wheat middlings | 10.0 |
| corn distillers dried solubles | 5.0 |
| fish meal with solubles | 5.0 |
| alfalfa meal, dehydrated (17%) | 2.5 |
| dicalcium phosphate, feed grade | 1.3 |
| calcium carbonate | 0.9 |
| vitamin premix [1] | 0.5 |
| salt (NaCl) | 0.3 |
| methionine hydroxy analog | 0.2 |
| trace mineral premix [2] | 0.1 |
| Total | 100.0 |

Pullet Grower

| Ingredients | Percent |
|---|---|
| corn, yellow, ground | 73.5 |
| soybean meal, solvent extracted, dehulled (50%) | 21.9 |
| dicalcium phosphate, feed grade | 2.5 |
| calcium carbonate | 1.0 |
| vitamin premix [1] | 0.5 |
| salt (NaCl) | 0.3 |
| methionine hydroxy analog | 0.2 |
| trace mineral premix [2] | 0.1 |
| Total | 100.0 |

Pullet Developer

| Ingredients | Percent |
|---|---|
| corn, yellow, ground | 67.4 |
| oats, ground whole | 15.0 |
| soybean meal, solvent extracted, dehulled (50%) | 13.4 |
| dicalcium phosphate, feed grade | 2.1 |
| calcium carbonate | 1.0 |
| vitamin premix [1] | 0.5 |
| methionine hydroxy analog | 0.3 |
| salt (NaCl) | 0.2 |
| trace mineral premix [2] | 0.1 |
| Total | 100.0 |

Layer, Light Breeds

| Ingredients | Percent |
|---|---|
| corn, yellow, ground | 61.00 |
| calcium carbonate | 8.50 |
| soybean meal, solvent extracted, dehulled (50%) | 8.25 |
| oats, ground whole | 5.00 |
| wheat middlings | 5.00 |
| corn distillers dried solubles | 5.00 |
| alfalfa meal, dehydrated (17%) | 2.50 |
| fish meal with solubles | 2.00 |
| dicalcium phosphate, feed grade | 1.60 |
| vitamin premix [1] | 0.50 |
| salt (NaCl) | 0.30 |
| methionine hydroxy analog | 0.25 |
| trace mineral premix [2] | 0.10 |

-continued
Layer, Light Breeds

| Ingredients | Percent |
|---|---|
| Total | 100.00 |

Pullet Grower, Broiler Breeders

| Ingredients | Percent |
|---|---|
| corn, yellow, ground | 38.1 |
| oats, ground whole | 30.0 |
| soybean meal, solvent extracted, dehulled (50%) | 12.8 |
| wheat middlings | 10.0 |
| alfalfa meal, dehydrated (17%) | 5.0 |
| dicalcium phosphate, feed grade | 1.7 |
| calcium carbonate | 1.3 |
| vitamin premix [1] | 0.5 |
| methionine hydroxy analog | 0.3 |
| salt (NaCl) | 0.2 |
| trace mineral premix [2] | 0.1 |
| Total | 100.0 |

Broiler Breeder

| Ingredients | Percent |
|---|---|
| corn, yellow, ground | 42.8 |
| oats, ground whole | 25.0 |
| soybean meal, solvent extracted, dehulled (50%) | 8.1 |
| wheat middlings | 5.0 |
| corn distillers dried solubles | 5.0 |
| fish meal with solubles | 2.5 |
| alfalfa meal, dehydrated (17%) | 2.5 |
| calcium carbonate | 6.3 |
| dicalcium phosphate, feed grade | 1.7 |
| vitamin premix [1] | 0.5 |
| salt (NaCl) | 0.3 |
| methionine hydroxy analog | 0.2 |
| trace mineral premix [2] | 0.1 |
| Total | 100.0 |

[1] vitamin premix provides 3000 IU of Vitamin A, 900 ICU of Vitamin D, 40 mg. of Vitamin E, 0.7 mg. of Vitamin K, 1000 mg. of choline, 70 mg. of niacin, 4 mg. of pantothenic acid, 4 mg. of riboflavin, 0.10 mg. of Vitamin $B_{12}$, 0.10 mg. of biotin and 125 mg. of ethoxyquin per kg. of complete feed.
[2] trace mineral premix provides 75 mg. of manganese, 50 mg. of zinc, 25 mg. of iron and 1 mg. of iodine per kg. of complete feed.

It will be understood that poultry feed compositions according to this invention will usually be made by first preparing a concentrated premix which contains the synergistic coccidiocides in high concentrations, such as from about 0.25 percent to about 80 percent. Such premixes comprise the coccidiocides dispersed in such physiologically-acceptable carriers as polyethylene glycols, propylene glycol, inert oils including vegetable oils and highly-refined mineral oils, ethanol, water, aqueous alcohols, vermiculite, diatomaceous earth, attapulgite, cracked corn, soybean meal, alfalfa meal, rice hulls, ground corncob, and the like.

The synergistic coccidiocides of this invention are also readily administered in the drinking water of poultry. They are incorporated into drinking water by merely adding a water-soluble or water-suspendible form of the compounds to water in the proper amount. Such compositions are most easily prepared by choosing a water-soluble form of the compounds. If an insoluble form is preferred, however, a suspension may be made. Suspensions are prepared by proper use of physiologically-acceptable adjuvants to keep the compounds in suspension in the water. Adjuvants are chosen from among the thickeners, such as carboxymethylcellulose, polyvinylpyrrolidone, gelatin and the alginates. Many classes of surfactants also serve to suspend the compounds. For example, lecithin, alkylphenol polyethylene oxide adducts, naphthalenesulfonates, alkylbenzenesulfonates, and the polyoxyethylene sorbitan esters are useful for preparing suspensions. It is usually most practical to prepare a concentrated suspension, or a dry formulation of the synergistic coccidiocides and suspending agents, which concentrated formulation is diluted in plain drinking water for administration to poultry.

It will be understood by both chemists and poultry scientists that the method of this invention may be combined with other methods of treating and nourishing poultry. For example, a composition according to the present invention may be further fortified or medicated with growth promoting agents, antibiotic drugs, parasiticides and the like without impairing the efficacy of the present invention.

While the primary thrust of this invention is the protection of poultry from coccidiosis, it will be apparent that other animals may be protected thereby, as well.

I claim:

1. A coccidiocidal composition for poultry comprising coccidiocidally-ineffective concentrations of monensin and of metichlorpindol, which coccidiocides are synergistically coccidiocidally effective in combination, together with a poultry feedstuff or drinking water, wherein the concentrations are from about 35 to 65 ppm. of monensin and from about 20 to about 70 ppm. of metichlorpindol, which concentrations are such that the combination is synergistic.

2. A composition of claim 1 wherein the concentrations are about 50 ppm. of monensin and from about 30 to about 60 ppm. of meticlorpindol.

3. A coccidiocidal method for treating poultry exposed to *Eimeria tenella* which comprises orally administering a composition of claim 1 to the poultry, wherein the composition supplies the poultry's entire food or drinking water supply.

4. The method of claim 3 wherein the poultry are chickens.

5. A coccidiocidal method for treating poultry exposed to *Eimeria tenella* which comprises orally administering a composition of claim 2 to the poultry, wherein the composition supplies the poultry's entire food or drinking water supply.

* * * * *

UNITED STATES PATENT OFFICE
CERTIFICATE OF CORRECTION

Patent No. 4,061,755　　　　　　　　　Dated December 6, 1977

Inventor(s) Larry R. McDougald

It is certified that error appears in the above-identified patent and that said Letters Patent are hereby corrected as shown below:

Column 8, line 3:　Change "35 to 65" to read -- 35 to about 65 --.

Signed and Sealed this

Twenty-second Day of August 1978

[SEAL]

Attest:

RUTH C. MASON
*Attesting Officer*

DONALD W. BANNER
*Commissioner of Patents and Trademarks*

Disclaimer 4,061,755.—*Larry R. McDougald*, Greenfield, Ind. COCCIDIOCIDAL COMBINATION OF MONENSIN AND METICHLORPINDOL. Patent dated Dec. 6, 1977. Disclaimer filed Aug. 8, 1983 by the assignee, *Eli Lilly and Co.*

Hereby enters this disclaimer to all claims of said patent.

[*Official Gazette September 20, 1983.*]